US009724081B2

(12) United States Patent
Phillips et al.

(10) Patent No.: US 9,724,081 B2
(45) Date of Patent: Aug. 8, 2017

(54) HEMOSTATIC SYSTEM AND ITS METHODS OF USE

(71) Applicant: Phillips Medical, LLC, Jefferson City, MO (US)

(72) Inventors: Victor Matthew Phillips, Jefferson City, MO (US); Royce Allen Simpson, Kokomo, IN (US)

(73) Assignee: Phillips Medical LLC, Jefferson City, MO (US)

( * ) Notice: Subject to any disclaimer, the term of this patent is extended or adjusted under 35 U.S.C. 154(b) by 904 days.

(21) Appl. No.: 13/909,744

(22) Filed: Jun. 4, 2013

(65) Prior Publication Data
US 2014/0358179 A1    Dec. 4, 2014

(51) Int. Cl.
*A61B 17/08* (2006.01)
*A61D 1/00* (2006.01)
*A61B 17/00* (2006.01)

(52) U.S. Cl.
CPC *A61B 17/0057* (2013.01); *A61B 2017/00407* (2013.01); *A61B 2017/00623* (2013.01); *A61B 2017/00654* (2013.01); *A61B 2017/00676* (2013.01); *A61B 2017/00778* (2013.01)

(58) Field of Classification Search
CPC ...... A61B 17/0057; A61B 2017/00637; A61B 17/00491; A61B 2017/0065; A61B 2017/00495; A61M 31/007; A61M 37/0069
USPC ............................. 606/213, 214, 218; 604/15
See application file for complete search history.

(56) References Cited

U.S. PATENT DOCUMENTS

| | | |
|---|---|---|
| 4,738,658 A | 4/1988 | Magro et al. |
| 4,850,960 A | 7/1989 | Grayzel |
| 4,890,612 A | 1/1990 | Kensey |
| 4,895,564 A | 1/1990 | Farrell |
| 4,929,246 A | 5/1990 | Sinofsky |
| 5,061,274 A | 10/1991 | Kensey |
| 5,108,421 A | 4/1992 | Fowler |
| 5,222,974 A | 6/1993 | Kensey et al. |
| 5,282,827 A | 2/1994 | Kensey et al. |
| 5,290,310 A | 3/1994 | Makower et al. |
| 5,306,254 A | 4/1994 | Nash et al. |
| 5,326,350 A | 7/1994 | Li |
| RE34,866 E | 2/1995 | Kensey et al. |
| 5,391,183 A | 2/1995 | Janzen et al. |
| 5,415,657 A | 5/1995 | Taymor-Luria |
| 5,431,639 A | 7/1995 | Shaw |

(Continued)

OTHER PUBLICATIONS

International Search Report and Written Opinion of PCT/US2011/032490; Jun. 29, 2011; 10 pages.

*Primary Examiner* — Katherine M Shi
(74) *Attorney, Agent, or Firm* — Armstrong Teasdale LLP

(57) ABSTRACT

A hemostatic system includes a first tube defining a first lumen configured to channel a fluid therethrough, a second tube housing at least a portion of the first tube and at least partially defining a second lumen configured to channel a hemocoagulant agent therethrough, a hopper coupled to the second tube, and an injection device. The hopper defines a cavity in fluid communication with the second lumen and is configured to retain the hemocoagulant agent therein. The injection device is selectively positionable within the second lumen and/or the cavity to facilitate channeling the hemocoagulant agent from the cavity through the second lumen.

15 Claims, 8 Drawing Sheets

(56) References Cited

U.S. PATENT DOCUMENTS

| | | |
|---|---|---|
| 5,437,292 A | 8/1995 | Kipshidze et al. |
| 5,437,631 A | 8/1995 | Janzen |
| 5,441,517 A | 8/1995 | Kensey et al. |
| 5,443,481 A | 8/1995 | Lee |
| 5,591,204 A | 1/1997 | Janzen et al. |
| 5,645,566 A | 7/1997 | Brenneman et al. |
| 5,653,730 A | 8/1997 | Hammerslag |
| 5,665,107 A | 9/1997 | Hammerslag |
| 5,676,689 A | 10/1997 | Kensey et al. |
| 5,707,393 A | 1/1998 | Kensey et al. |
| 5,716,375 A | 2/1998 | Fowler |
| 5,725,498 A | 3/1998 | Janzen et al. |
| 5,741,223 A | 4/1998 | Janzen et al. |
| 5,766,157 A | 6/1998 | Tilton, Jr. |
| 5,766,206 A | 6/1998 | Wijkamp et al. |
| 5,782,861 A | 7/1998 | Cragg et al. |
| 5,843,124 A | 12/1998 | Hammerslag |
| 5,868,762 A | 2/1999 | Cragg et al. |
| 5,935,147 A | 8/1999 | Kensey et al. |
| 5,951,583 A | 9/1999 | Jensen et al. |
| 5,984,950 A | 11/1999 | Cragg et al. |
| 6,045,570 A | 4/2000 | Epstein et al. |
| 6,056,768 A | 5/2000 | Cates et al. |
| 6,090,130 A | 7/2000 | Nash et al. |
| 6,296,657 B1 | 10/2001 | Brucker |
| 6,302,898 B1 | 10/2001 | Edwards et al. |
| 6,315,753 B1 | 11/2001 | Cragg et al. |
| 6,325,789 B1 | 12/2001 | Janzen et al. |
| 6,371,974 B1 | 4/2002 | Brenneman et al. |
| 6,371,975 B2 | 4/2002 | Cruise et al. |
| 6,527,734 B2 | 3/2003 | Cragg et al. |
| 6,544,236 B1 | 4/2003 | Cragg et al. |
| 6,547,806 B1 | 4/2003 | Ding |
| 6,610,026 B2 | 8/2003 | Cragg et al. |
| 6,676,664 B1* | 1/2004 | Al-Assir ............ A61B 17/8819 606/92 |
| 6,743,248 B2 | 6/2004 | Edwards et al. |
| 6,830,756 B2 | 12/2004 | Hnojewyj |
| 6,863,680 B2 | 3/2005 | Ashby |
| 6,984,219 B2 | 1/2006 | Ashby et al. |
| 7,029,489 B1 | 4/2006 | Ashby et al. |
| 7,037,322 B1 | 5/2006 | Sing et al. |
| 7,048,710 B1 | 5/2006 | Cragg et al. |
| 7,201,725 B1 | 4/2007 | Cragg et al. |
| 7,318,933 B2 | 1/2008 | Hnojewyj |
| 7,335,219 B1 | 2/2008 | Ashby et al. |
| 7,455,680 B1 | 11/2008 | Ashby et al. |
| 7,611,479 B2 | 11/2009 | Cragg et al. |
| 7,625,352 B1 | 12/2009 | Ashby et al. |
| 8,845,580 B2* | 9/2014 | Gellman ............ A61M 5/2066 604/218 |
| 2001/0018598 A1 | 8/2001 | Cruise et al. |
| 2003/0009194 A1* | 1/2003 | Saker ............... A61B 17/00491 606/213 |
| 2003/0088271 A1 | 5/2003 | Cragg et al. |
| 2003/0093116 A1* | 5/2003 | Nowakowski ... A61B 17/00491 606/215 |
| 2003/0100921 A1 | 5/2003 | Addis et al. |
| 2004/0019328 A1 | 1/2004 | Sing et al. |
| 2004/0098024 A1 | 5/2004 | Dieck et al. |
| 2004/0102730 A1 | 5/2004 | Davis et al. |
| 2004/0193170 A1* | 9/2004 | Kemppainen ...... A61B 17/8822 606/92 |
| 2006/0100664 A1 | 5/2006 | Pai et al. |
| 2007/0038245 A1 | 2/2007 | Morris et al. |
| 2007/0123816 A1* | 5/2007 | Zhu .................... A61B 17/0206 604/57 |
| 2008/0038313 A1 | 2/2008 | Addis et al. |
| 2008/0046005 A1 | 2/2008 | Lenker et al. |
| 2008/0071310 A1 | 3/2008 | Hoffman et al. |
| 2008/0082122 A1 | 4/2008 | Khosravi et al. |
| 2008/0161849 A1 | 7/2008 | Cates et al. |
| 2009/0088793 A1 | 4/2009 | Bagaoisan et al. |
| 2009/0137965 A1* | 5/2009 | Kim .................. A61B 17/8822 604/208 |
| 2009/0143808 A1 | 6/2009 | Houser |
| 2009/0171282 A1 | 7/2009 | Pipenhagen et al. |
| 2009/0275916 A1* | 11/2009 | Harms .................... A61M 5/24 604/506 |
| 2010/0249720 A1* | 9/2010 | Biyani .................. A61F 2/4601 604/218 |
| 2011/0106064 A1* | 5/2011 | Zou .................... A61M 5/14276 604/891.1 |
| 2011/0137338 A1* | 6/2011 | Phillips ............. A61B 17/0057 606/213 |
| 2011/0282381 A1* | 11/2011 | Cronin ............... A61B 10/0275 606/213 |
| 2014/0135824 A1* | 5/2014 | Terwey ............. A61B 17/0057 606/213 |

\* cited by examiner

HEMOSTATIC SYSTEM AND ITS METHODS OF USE

BACKGROUND OF THE INVENTION

The subject matter described herein relates generally to medical devices and, more particularly, to a hemostatic system.

Catheter introducers are known to provide access to an artery for at least some medical procedures including, without limitation, cardiac catheterizations and peripheral endovascular procedures. After conducting such medical procedures, the catheter introducer is removed from the access site, leaving an arterial opening. At least some body fluids including, without limitation, blood are discharged from the arterial opening. Excess blood loss may endanger and/or traumatize the patient. One known method of controlling blood loss is through direct manual pressure over the arterial opening.

BRIEF SUMMARY OF THE INVENTION

In one aspect, a method is provided for sealing a puncture of a vessel using a hemostatic system that includes a first tube defining a first lumen, a second tube housing at least a portion of the first tube and at least partially defining a second lumen, a hopper coupled to the second tube and defining a cavity in fluid communication with the second lumen, and an injection device. The method includes retaining a hemocoagulant agent in the cavity defined by the hopper, advancing the first tube into the vessel until a fluid is channeled through the first lumen defined by the first tube, and selectively positioning the injection device within at least one of the cavity and the second lumen defined at least partially by the second tube to channel the hemocoagulant agent from the cavity through the second lumen.

In another aspect, a hemostatic system is provided for sealing a puncture of a vessel. The hemostatic system includes a first tube defining a first lumen configured to channel a fluid therethrough, a second tube housing at least a portion of the first tube and at least partially defining a second lumen configured to channel a hemocoagulant agent therethrough, a hopper coupled to the second tube, and an injection device. The hopper defines a cavity in fluid communication with the second lumen and is configured to retain the hemocoagulant agent therein. The injection device is selectively positionable within the second lumen and/or the cavity to facilitate channeling the hemocoagulant agent from the cavity through the second lumen.

In yet another aspect, a hemostatic system is provided for sealing a puncture of a vessel. The hemostatic system includes a first tube defining a first lumen configured to channel a fluid therethrough, a second tube housing at least a portion of the first tube and at least partially defining a second lumen configured to channel a hemocoagulant agent therethrough, an auger extending through the second lumen, and a wheel coupled to the auger to facilitate rotating the auger within the second lumen.

The features, functions, and advantages described herein may be achieved independently in various embodiments of the present disclosure or may be combined in yet other embodiments, further details of which may be seen with reference to the following description and drawings.

DETAILED DESCRIPTION OF THE INVENTION

The methods and apparatus described herein relate to medical devices and, more particularly, to a hemostatic system for use in sealing a puncture of a vessel. The hemostatic system described herein facilitates sealing an opening of a blood vessel. More particularly, in at least one embodiment, the hemostatic system includes a first tube defining a first lumen, a second tube at least partially defining a second lumen, a hopper at least partially defining a cavity, and an injection device selectively positionable within the second lumen and/or the cavity to facilitate channeling a hemocoagulant agent from the cavity through the second lumen. The hemocoagulant agent is discharged from the second lumen and seals the opening to reduce a time required for hemostasis and/or ambulation.

As used herein, an element or step recited in the singular and preceded with the word "a" or "an" should be understood as not excluding plural said elements or steps, unless such exclusion is explicitly stated. Further, references to "one embodiment" are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Figure 1:
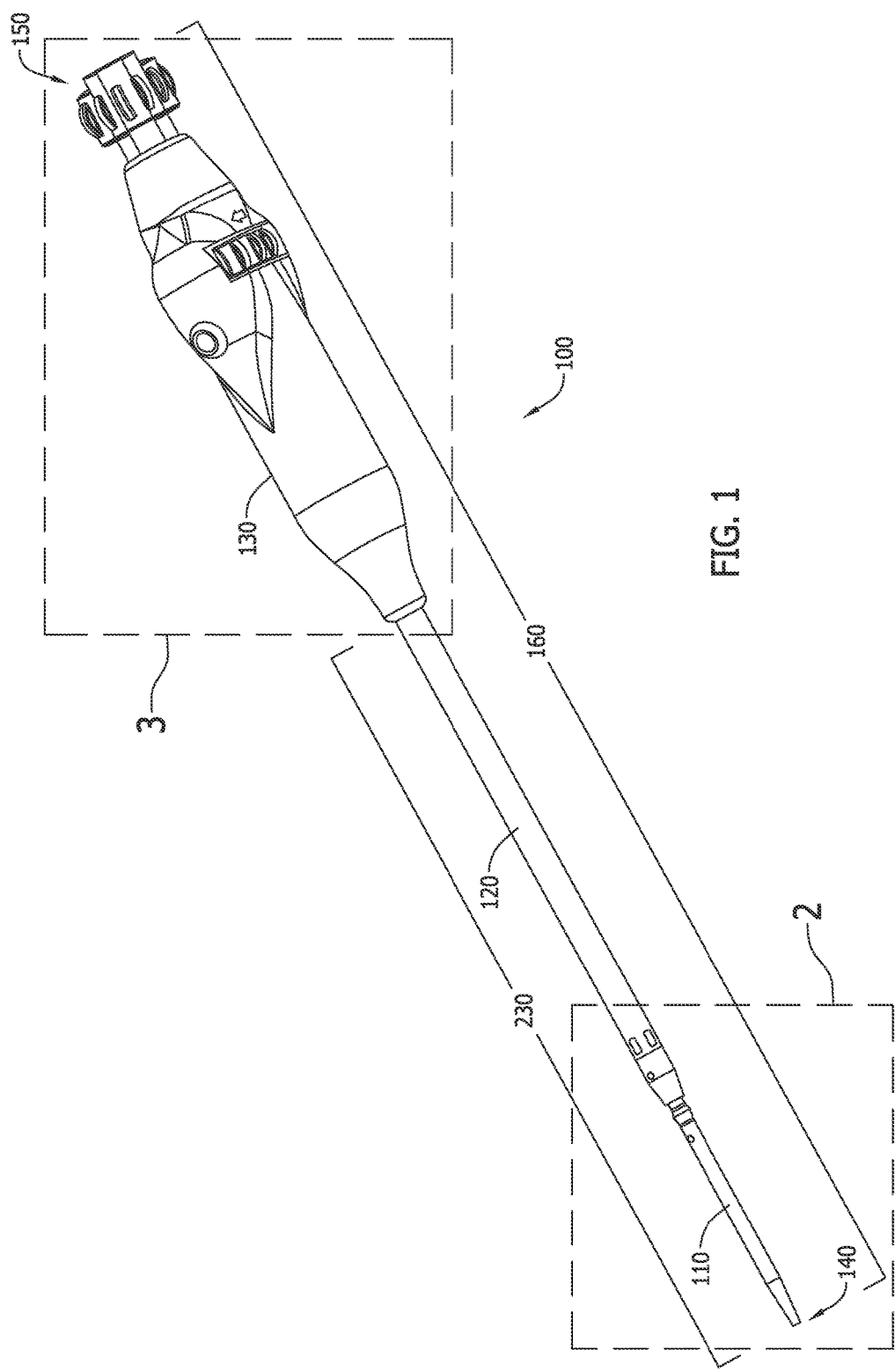
FIG. 1 is a perspective view of an exemplary hemostatic system.

FIG. 1 is a perspective view of an exemplary hemostatic system 100 for sealing a puncture of a vessel (not shown). In the exemplary embodiment, hemostatic system 100 includes a first or inner tube 110, a second or outer tube 120, and a hopper 130 coupled to outer tube 120. In the exemplary embodiment, hemostatic system 100 has a distal end 140, a proximal end 150, and a length 160. In the exemplary embodiment, length 160 is at least approximately 5 inches (in.). More particularly, in the exemplary embodiment, length 160 is between approximately 8 in. and approximately 12 in. Even more particularly, length 160 is approximately 10.147 in. Alternatively, hemostatic system 100 may have any length that enables the methods and systems to function as described herein. In the exemplary embodiment, a distal end of inner tube 110 is tapered to facilitate traversing through subcutaneous tissue and into a lumen of the vessel.

Figure 2:
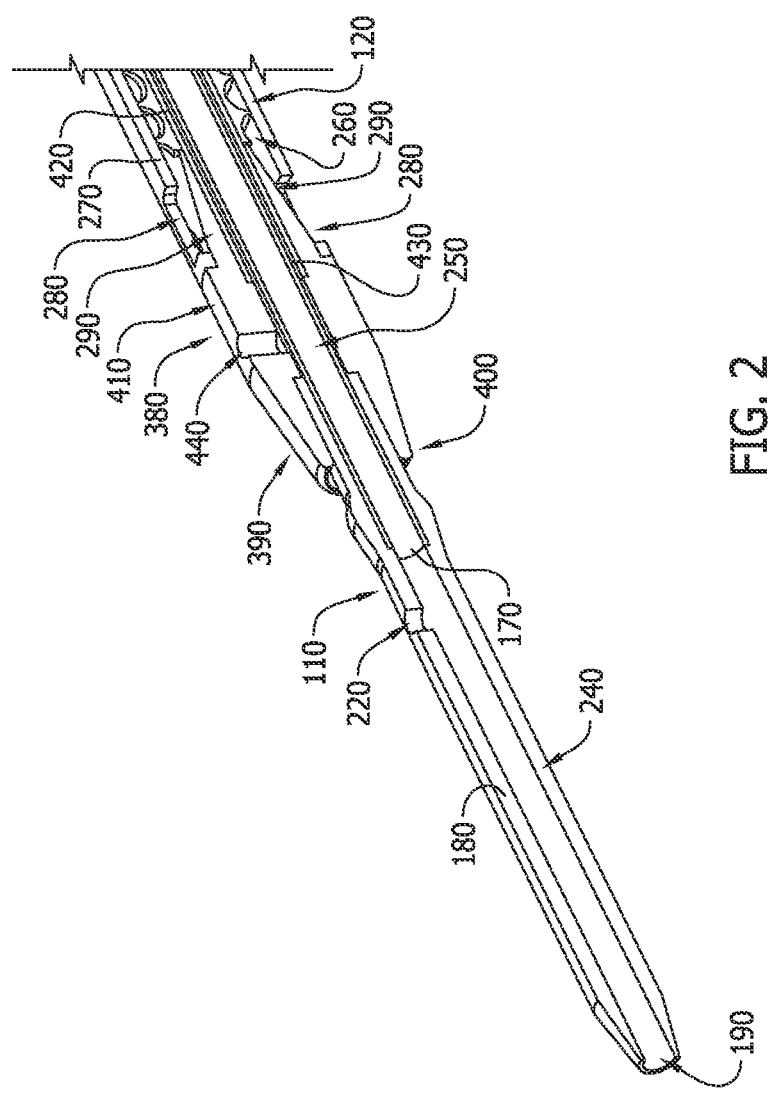
FIG. 2 is a cross-sectional view of a distal portion of the hemostatic system shown in FIG. 1.
Figure 3:
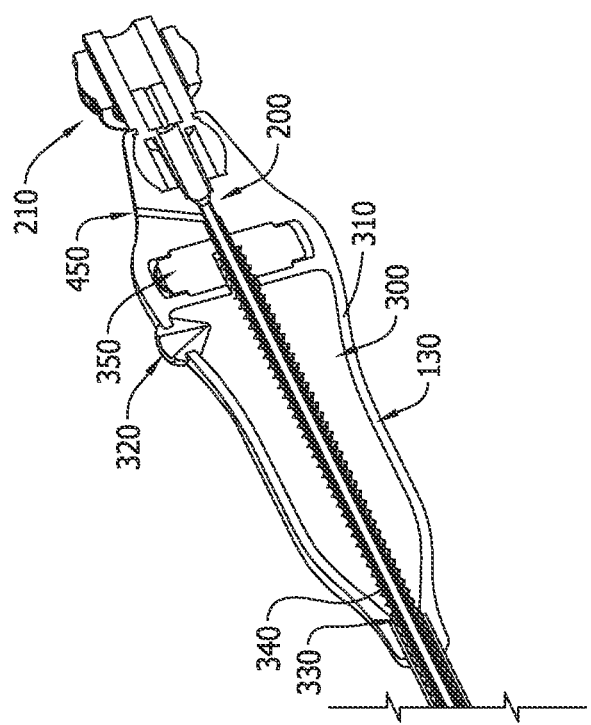
FIG. 3 is a cross-sectional view of a proximal portion of the hemostatic system shown in FIG. 1.

FIGS. 2 and 3 are cross-sectional views of hemostatic system 100. In the exemplary embodiment, inner tube 110 defines a first lumen 170 configured to channel blood or, more broadly, a fluid therethrough. More specifically, in the exemplary embodiment, inner tube 110 includes a sidewall 180 that defines first lumen 170 and includes a first opening 190 at a distal end of first lumen 170, and a second opening 200 at a proximal end of first lumen 170. In the exemplary embodiment, first opening 190 is sized to receive a guidewire (not shown), and second opening 200 is sized to channel the fluid through first lumen 170 about the guidewire. First opening 190 and/or second opening 200 may have any size, shape, and/or configuration that enables inner tube 110 to function as described herein.

In the exemplary embodiment, a valve 210 proximate to second opening 200 is selectively movable between an open configuration and a closed configuration. More particularly, in the exemplary embodiment, valve 210 is actuatable towards the closed configuration to selectively restrict access to second opening 200 and/or first lumen 170. That is, in the exemplary embodiment, valve 210 enables second opening 200 to be at least partially closed such that a flow of the fluid through first lumen 170 is decreased. Moreover, in the exemplary embodiment, valve 210 is actuatable towards the open configuration to selectively provide access to second opening 200 and/or first lumen 170. That is, in the exemplary embodiment, valve 210 enables second opening 200 to be at least partially opened such that a flow of the fluid through first lumen 170 is increased.

In the exemplary embodiment, inner tube 110 includes a side opening 220 extending through sidewall 180 that is in fluid communication with first lumen 170 such that fluid may enter first lumen 170 through side opening 220. In the exemplary embodiment, a distance 230 (shown in FIG. 1) between side opening 220 and a distal end of hopper 130 is at least approximately 2 in. More particularly, in the exemplary embodiment, distance 230 is between approximately 3 in. and approximately 6 in. Even more particularly, distance 230 is approximately 4.2 in. Alternatively, hemostatic system 100 may have any distance between side opening 220 and hopper 130 that enables the methods and systems to function as described herein.

In the exemplary embodiment, inner tube 110 includes a distal portion 240 and a proximal portion 250 coupled to distal portion 240 by an interference fit. Alternatively, inner tube 110 may include any number of portions, and/or the portions may be coupled in any configuration and/or using any mechanism that enables inner tube 110 to function as described herein. In the exemplary embodiment, outer tube 120 houses proximal portion 250 of inner tube 110, and distal portion 240 is generally exposed. That is, in the exemplary embodiment, outer tube 120 does not house distal portion 240 of inner tube 110.

In the exemplary embodiment, outer tube 120 at least partially defines a second lumen 260 configured to channel a hemocoagulant agent therethrough. More specifically, in the exemplary embodiment, outer tube 120 includes a sidewall 270 that at least partially defines second lumen 260. In one implementation, the hemocoagulant agent is a FDA-approved powdered hemocoagulant agent. Alternatively, the hemocoagulant agent may be any substance and/or composition that enables outer tube 120 to function as described herein.

In the exemplary embodiment, outer tube 120 includes at least one side opening 280 extending through sidewall 270 that is in fluid communication with second lumen 260 such that hemocoagulant agent channeled through second lumen 260 is dischargeable through side opening 280. More specifically, in the exemplary embodiment, a plurality of side openings 280 are circumferentially spaced about sidewall 270 proximate to a distal end of outer tube 120. For example, in one implementation, outer tube 120 includes six side openings 280 extending through sidewall 270 that are circumferentially spaced about outer tube 120. Alternatively, outer tube 120 may include any number of side openings that enables outer tube 120 to function as described herein.

In the exemplary embodiment, a separating mechanism 290 proximate to side opening 280 facilitates separating and/or breaking up the hemocoagulant agent as it is channeled through side opening 280. In at least some implementations, separating mechanism 290 is configured to separate at least some of the hemocoagulant agent within second lumen 260 from a fluid to facilitate reducing a coagulation of the hemocoagulant agent within second lumen 260. In the exemplary embodiment, separating mechanism 290 includes a plurality of blades circumferentially spaced within second lumen 260 and extending radially outward from a center axis of hemostatic system 100. For example, in one implementation separating mechanism 290 includes four blades that are circumferentially spaced about inner tube 110. Alternatively, separating mechanism 290 may include any number of blades and/or use any device or method that enables outer tube 120 to function as described herein.

In the exemplary embodiment, hopper 130 defines a cavity 300 configured to retain the hemocoagulant agent therein. In the exemplary embodiment, cavity 300 is sized to retain at least approximately 2 milliliters (mL) of powder. More particularly, cavity 300 is sized to retain between approximately 4 mL and 7 mL of powder. Even more particularly, cavity 300 is sized to retain approximately 5 mL of powder. Alternatively, cavity 300 may be sized to retain any quantity of hemocoagulant agent that enables outer tube 120 to function as described herein.

In the exemplary embodiment, hopper 130 includes a sidewall 310 that defines cavity 300 and includes a side opening 320 extending through sidewall 310. In the exemplary embodiment, cavity 300 is in fluid communication with second lumen 260 and side opening 320 such that hemocoagulant agent loaded through side opening 320 may be stored within cavity 300 and/or channeled through second lumen 260.

In the exemplary embodiment, an injection device 330 is selectively positionable within second lumen 260 and/or cavity 300 to facilitate channeling the hemocoagulant agent from cavity 300 through second lumen 260. In the exemplary embodiment, injection device 330 includes an auger 340 extending through second lumen 260 and/or cavity 300. More specifically, in the exemplary embodiment auger 340 is a substantially helical body (e.g., a substantially laterally-extending blade) extending about inner tube 110 such that a rotation of the helical body channels hemocoagulant agent through second lumen 260.

Figure 4:
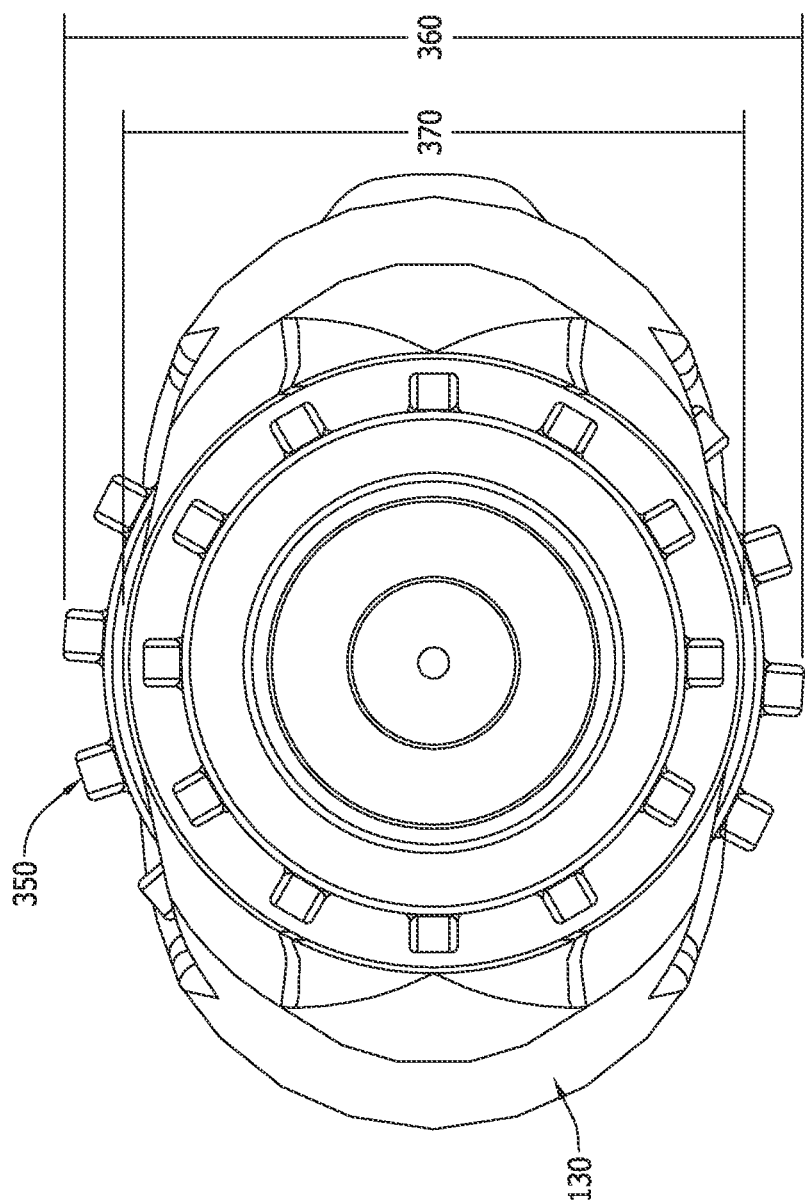
FIG. 4 is an end view of the hemostatic system shown in FIG. 1.

Moreover, in the exemplary embodiment, injection device 330 includes a wheel 350 coupled to auger 340 to facilitate rotating auger 340 within second lumen 260 and/or cavity 300. More specifically, in the exemplary embodiment, auger 340 is selectively rotatable in a first direction (e.g., a clockwise direction when looking from proximal end 150 towards distal end 140 as shown in FIG. 4) to channel the hemocoagulant agent through second lumen 260. That is, in the exemplary embodiment, when auger 340 is rotated in the first direction, the hemocoagulant agent is "pushed" by the substantially laterally-extending blade and/or channeled downstream from cavity 300 and/or through second lumen 260 towards side openings 280.

As shown in FIG. 4, wheel 350 has a diameter 360 that is greater than and/or equal to a width 370 of hopper 130. In at least some embodiments, a seal fabricated at least partially from a silicone, for example, is positioned at a distal end of cavity 300 to facilitate retaining the hemocoagulant agent within cavity 300. Alternatively, any material may be used that enables hopper 130 to function as described herein.

In the exemplary embodiment, hemostatic system 100 includes a plug 380 that at least partially circumscribes inner tube 110 and/or outer tube 120. In the exemplary embodiment, plug 380 is positioned with respect to inner tube 110 and/or outer tube 120 such that plug 380 and/or side opening 280 of outer tube 120 are positionable outside and substantially adjacent the vessel when side opening 220 of inner tube 110 is within the lumen of the vessel.

In the exemplary embodiment, plug 380 is fabricated at least partially from a soft and/or pliable material that enables a seal to be provided at the vessel and/or access site. For example, plug 380 may be fabricated from, without limitation, rubber and/or a rubber-like material. In the exemplary embodiment, plug 380 includes a distal portion 390 having a distal apex 400 oriented towards the distal end of hemostatic system 100, and a proximal portion 410. In the exemplary embodiment, distal portion 390 is substantially cone-shaped to facilitate traversing plug 380 through subcutaneous tissue.

In the exemplary embodiment, hemostatic system 100 includes a third or intermediate tube 420 positioned radially between inner tube 110 and outer tube 120. More specifically, in the exemplary embodiment, intermediate tube 420 is positioned such that second lumen 260 is defined between intermediate tube 420 and outer tube 120, and a third lumen 430 configured to channel blood or, more broadly, a fluid therethrough is defined between intermediate tube 420 and inner tube 110. In the exemplary embodiment, third lumen 430 is in fluid communication with a first opening 440 extending through plug 380 and a second opening 450 extending through hopper 130 such that fluid may enter third lumen 430 through first opening 440 and is dischargeable through second opening 450.

Figure 5:
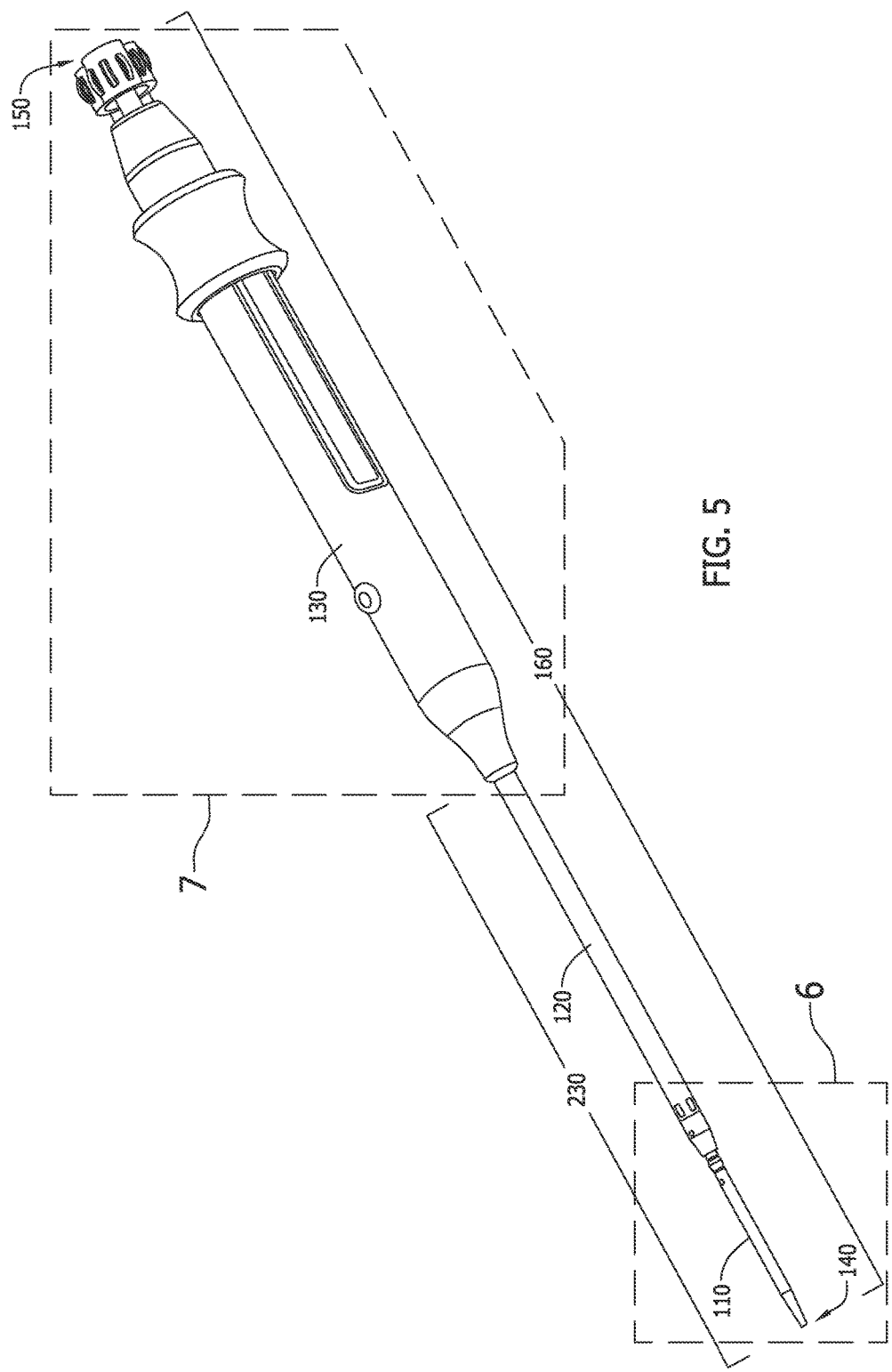
FIG. 5 is a perspective view of another exemplary hemostatic system.
Figure 6:
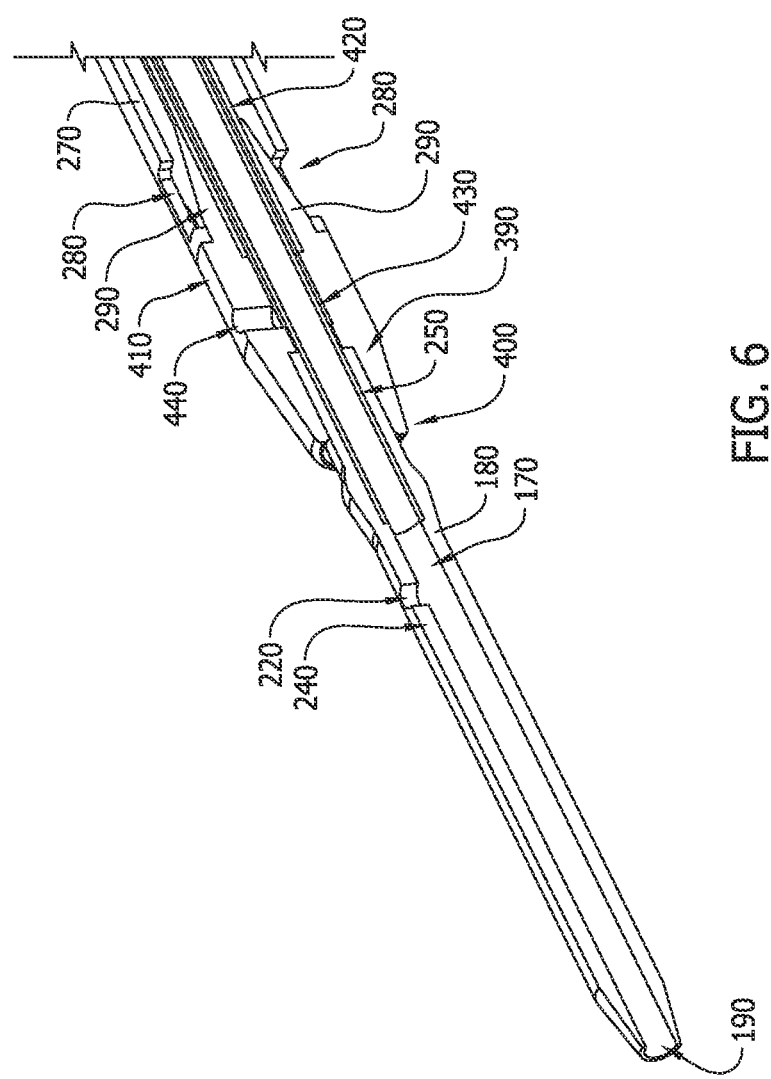
FIG. 6 is a cross-sectional view of a distal portion of the hemostatic system shown in FIG. 5.
Figure 7:
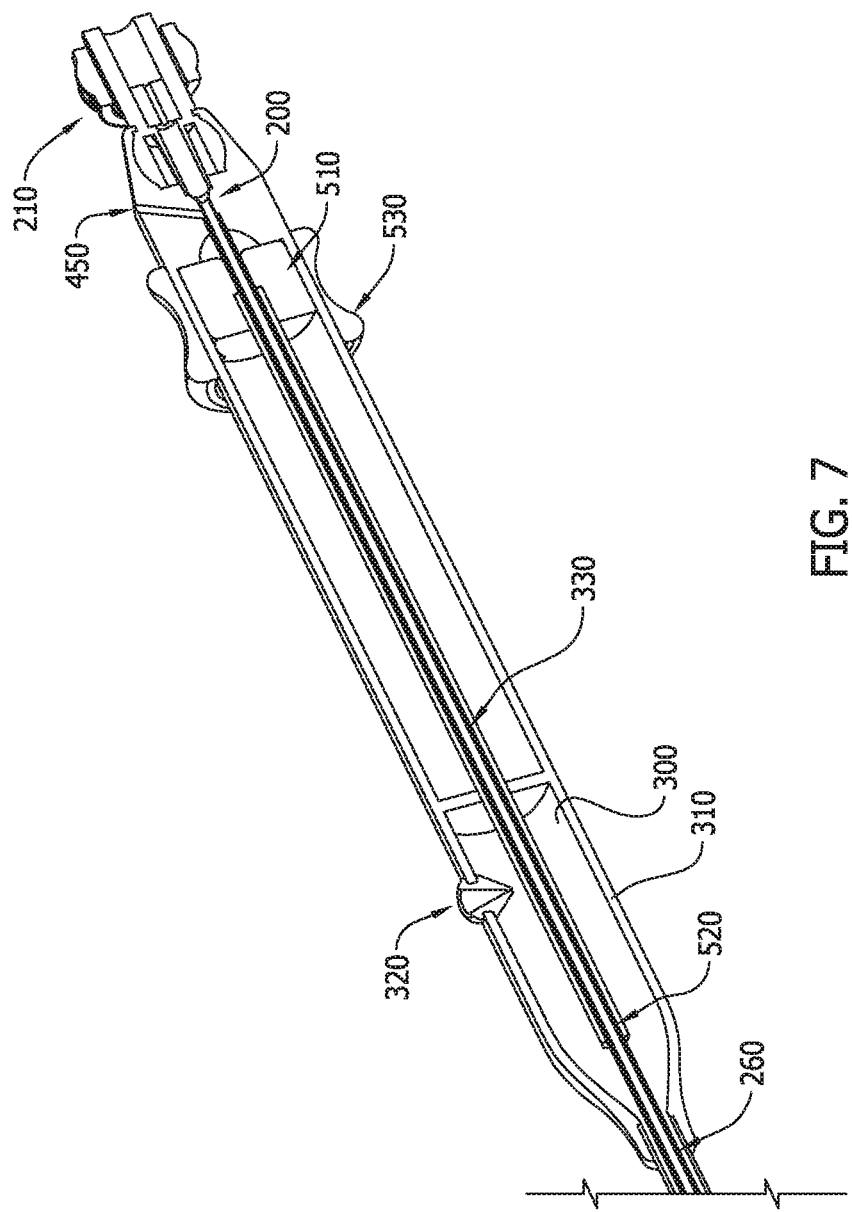
FIG. 7 is a cross-sectional view of a proximal portion of the hemostatic system shown in FIG. 5.

FIG. 5 is a perspective view of another exemplary hemostatic system 500 for sealing a puncture of a vessel (not shown). FIGS. 6 and 7 are cross-sectional views of hemostatic system 500. Hemostatic system 500 is substantially similar to hemostatic system 100 and, in the absence of a contrary representation, the same reference numbers identify the same or similar elements.

In the exemplary embodiment, an injection device 510 is selectively positionable within second lumen 260 and/or cavity 300 to facilitate channeling the hemocoagulant agent from cavity 300 through second lumen 260. In the exemplary embodiment, injection device 510 includes a plunger 520 extending through second lumen 260 and/or cavity 300. More specifically, in the exemplary embodiment plunger 520 is a substantially cylindrical body extending about inner tube 110 such that a translation of the helical body channels hemocoagulant agent through second lumen 260.

Moreover, in the exemplary embodiment, injection device 510 includes a handle 530 coupled to plunger 520 to facilitate moving and/or translating plunger 520 within second lumen 260 and/or cavity 300 between a first or proximal position and a second or distal position. More specifically, in the exemplary embodiment, plunger 520 is selectively translatable towards the distal position to facilitate discharging the hemocoagulant agent from second lumen 260 and/or side opening 280. Moreover, in the exemplary embodiment, plunger 520 is selectively translatable towards the proximal position to facilitate loading the hemocoagulant agent into second lumen 260. That is, in the exemplary embodiment, when plunger 520 is in the proximal position, second lumen 260 is "open" such that plunger 520 is clear of and/or outside second lumen 260 and hemocoagulant agent within cavity 300 is free to fall into second lumen 260 and, when plunger is advanced through second lumen 260, the hemocoagulant agent within second lumen 260 is "pushed" by plunger 520 and/or channeled downstream through second lumen 260 towards side openings 280.

Figure 8:
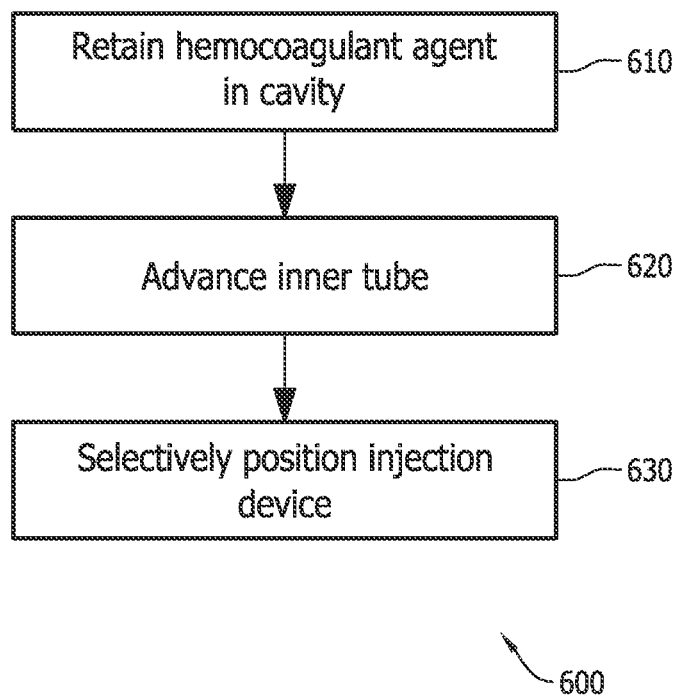
FIG. 8 is a flow chart illustrating an exemplary method of using the hemostatic system shown in FIG. 1 or 5.

FIG. 8 is a flow chart illustrating an exemplary method 600 of using hemostatic system 100 and/or 500 to seal a puncture of an artery or vessel with a powdered hemocoagulant agent. To prepare hemostatic system 100 and/or 500 for use, in the exemplary embodiment, the powdered hemocoagulant agent is loaded through hopper side opening 320 and/or retained 610 within cavity 300. During operation, in the exemplary embodiment, inner tube 110 is aligned such that a guidewire (not shown) extends through first opening 190 and second opening 200, and inner tube 110 is advanced 620 along the guidewire through subcutaneous tissue until blood is channeled through first lumen 170 and/or discharged from second opening 200.

In the exemplary embodiment, the blood discharge (i.e., reflux) from second opening 200 is a visual indication that inner tube side opening 220 is positioned within the vessel and/or outer tube side opening 280. Moreover, in the exemplary embodiment, plug 380 provides a tactile indication that plug 380 and/or outer tube side opening 280 is positioned outside and substantially adjacent the vessel and/or inner tube side opening 220 is positioned within the vessel.

In the exemplary embodiment, valve 210 is moved towards the closed configuration to restrict access to second opening 200 and/or facilitate reducing blood flow through first lumen 170. In at least some implementations, hemostatic system 100 is advanced along the guidewire too far through subcutaneous tissue. In such an implementation, the blood enters plug opening 440, is channeled through intermediate tube 420, and/or is discharged from hopper opening 450. In such an implementation, the blood discharge from hopper opening 450 is a visual indication that hemostatic system 100 is advanced too far through subcutaneous tissue and/or should be at least partially withdrawn from the subcutaneous tissue until blood does not discharge from hopper opening 450.

In the exemplary embodiment, injection device 330 is selectively positioned 630 within second lumen 260 and/or cavity 300 to channel the hemocoagulant agent from cavity 300 through second lumen 260 and/or discharge the hemocoagulant agent from side opening 280. For example, when using hemostatic system 100, the hemocoagulant agent is channeled from cavity 300 through second lumen 260 as auger 340 is rotated in the first direction within second lumen 260 and/or cavity 300. In such an embodiment, the hemocoagulant agent is gravity fed into auger 340 as it is rotated in the clockwise direction. For another example, when using hemostatic system 500, the hemocoagulant agent is channeled from cavity 300 through second lumen 260 as plunger 520 is translated towards the distal position. In such an embodiment, the hemocoagulant agent is gravity fed into second lumen 260 when plunger 520 is translated towards the proximal position. That is, in such an embodiment, plunger 520 may be systematically translated between the proximal position and the distal position to inject a desired amount of hemocoagulant agent.

In the exemplary embodiment, as the hemocoagulant agent is discharged from side opening 280, separating mechanism 290 separates and/or breaks up at least some of the hemocoagulant agent. In at least some embodiments, the injection device is selectively positioned 630 as hemostatic system 100 is systematically withdrawn from the subcutaneous tissue. In at least some embodiments, direct, non-occlusive manual pressure is continuously applied to the access site after hemostatic system 100 is withdrawn from the subcutaneous tissue until hemostasis is achieved.

The methods and apparatus described herein relate to medical devices and, more particularly, to a hemostatic system. The hemostatic system described herein facilitates sealing, for example, an arterial opening. The exemplary hemostatic system includes a first tube defining a first lumen configured to channel a fluid therethrough, a second tube housing at least a portion of the first tube and at least partially defining a second lumen configured to channel a hemocoagulant agent therethrough, a hopper coupled to the second tube, and an injection device. The injection device is selectively positionable within the second lumen and/or the cavity to facilitate channeling the hemocoagulant agent from the cavity through the second lumen. The powdered hemocoagulant agent facilitates sealing the arterial opening to reduce a time required for hemostasis and/or ambulation.

Exemplary embodiments of medical devices are described above in detail. The methods and systems are not limited to the specific embodiments described herein, but rather, operations of the methods and components of the systems may be utilized independently and separately from other operations and/or components described herein. For example, the methods and apparatus described herein may have other industrial and/or consumer applications and are not limited to practice with medical devices as described herein. Rather, one or more embodiments may be implemented and utilized in connection with other industries.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for sealing a puncture of a vessel using a hemostatic system that includes (i) a first tube including a first sidewall and a first side opening extending through the first sidewall, the first sidewall defining a first lumen, (ii) a second tube housing at least a portion of the first tube and at least partially defining a second lumen, the second tube including a second opening in fluid communication with the second lumen, (iii) a hopper coupled to the second tube and defining a cavity in fluid communication with the second lumen, (iv) an injection device, and (v) a plug that at least partially circumscribes the first tube, said method comprising:

retaining a hemocoagulant agent in the cavity defined by the hopper;

advancing the first tube into the vessel until a fluid is channeled into the first side opening and through the first lumen defined by the first tube, wherein the plug is spaced proximally from the first side opening such that the plug is substantially adjacent the vessel when the first side opening is positioned within a lumen of the vessel, and wherein the second opening is spaced proximally from the first side opening such that the second opening is outside the vessel when the fluid is channeled into the first side opening; and selectively positioning the injection device within at least one of the cavity and the second lumen such that a hemocoagulant agent is channeled from the cavity through the second lumen and out the second opening.

2. A method in accordance with claim 1 further comprising loading the hemocoagulant into the cavity through an opening extending through a sidewall of the hopper.

3. A method in accordance with claim 1, wherein the step of advancing the first tube further comprises:
advancing a guidewire towards the vessel;
advancing the first tube along the guidewire towards the vessel until an opening extending through a sidewall of the first tube is positioned within the vessel such that the fluid is channeled through the opening; and
moving a valve to selectively restrict the fluid from being channeled through the first lumen.

4. A method in accordance with claim 1, wherein selectively positioning an injection device further comprises rotating the injection device within the second lumen to facilitate channeling the hemocoagulant agent from the cavity through the second lumen.

5. A method in accordance with claim 1, wherein the step of selectively positioning the injection device further comprises translating the injection device within at least one of the second lumen and the cavity to facilitate channeling the hemocoagulant agent from the cavity through the second lumen.

6. A method in accordance with claim 1 further comprising:
separating at least some of the hemocoagulant agent using a separating mechanism within the second lumen; and
discharging the hemocoaaulant agent through a plurality of side openings that extend through a sidewall of the second tube.

7. A method in accordance with claim 1, wherein the step of advancing the first tube further comprises:
advancing a third tube into the vessel until a fluid is channeled through a third lumen at least partially defined by the third tube; and
withdrawing the third tube until the fluid is not channeled through the third lumen.

8. A hemostatic system for sealing a puncture of a vessel, said hemostatic system comprising:
a first tube comprising a first sidewall and a first side opening extending through said first sidewall, said first sidewall defining a first lumen configured to channel a fluid therethrough, said first side opening in flow communication with said first lumen;
a second tube housing at least a portion of said first tube and at least partially defining a second lumen configured to channel a hemocoagulant agent therethrough, said second tube comprising a second opening in fluid communication with said second lumen, said second opening is spaced proximally from said first side opening such that said second opening is positionable outside and substantially adjacent the vessel when said first side opening is positioned within a lumen of the vessel;
a hopper coupled to said second tube, said hopper defining a cavity in fluid communication with said second lumen and configured to retain the hemocoagulant agent therein;
an injection device selectively positionable within at least one of said second lumen and said cavity to facilitate channeling the hemocoagulant agent from said cavity through said second lumen and out said second opening; and a plug that at least partially circumscribes said first tube, said plug is spaced proximally from said first side opening such that said plug is positionable substantially adjacent the vessel when said first side opening is positioned within a lumen of the vessel.

9. A hemostatic system in accordance with claim 8, wherein said first tube further comprises a distal opening at a distal end of said first lumen and a proximal opening at a proximal end of said first lumen, said first sidewall extends from said distal end to said proximal end.

10. A hemostatic system in accordance with claim 9 further comprising a valve proximate to said proximal opening, said valve selectively movable between an open configuration and a closed configuration.

11. A hemostatic system in accordance with claim 8, wherein said second opening comprises a plurality of second openings, said system further comprising a separating mechanism proximate to the plurality of side openings.

12. A hemostatic system in accordance with claim 8, wherein said hopper includes a sidewall and a hopper side opening extending through said sidewall, said hopper side opening in communication with said second lumen.

13. A hemostatic system in accordance with claim 8, wherein said injection device comprises:
   an auger extending through said second lumen; and
   a wheel coupled to said auger to facilitate rotating said auger within said second lumen.

14. A hemostatic system in accordance with claim 8, wherein said injection device comprises:
   a plunger positionable within at least one of said second lumen and said cavity; and
   a handle coupled to said plunger to facilitate translating said plunger within at least one of said second lumen and said cavity.

15. A hemostatic system in accordance with claim 8, further comprising a third tube positioned radially between said first tube and said second tube, said third tube at least partially defining a third lumen configured to channel the fluid therethrough, said third lumen is in fluid communication with a third opening extending through said plug, said third opening is positioned between said first side opening and said second opening.

\* \* \* \* \*